United States Patent [19]

Greer

[11] Patent Number: 4,894,364

[45] Date of Patent: Jan. 16, 1990

[54] METHOD AND MATERIALS FOR SENSITIZING NEOPLASTIC TISSUE TO RADIATION

[76] Inventor: Sheldon B. Greer, 8320 SW 86 Ter., Miami, Fla. 33143

[21] Appl. No.: 749,540

[22] PCT Filed: Oct. 26, 1984

[86] PCT No.: PCT/US84/01735

§ 371 Date: Oct. 26, 1984

§ 102(e) Date: Jan. 1, 1901

[87] PCT Pub. No.: WO85/01871

PCT Pub. Date: May 9, 1985

Related U.S. Application Data

[63] Continuation-in-part of Ser. No. 545,693, Oct. 26, 1983, abandoned.

[51] Int. Cl.⁴ .................. A61B 19/00; C07H 17/00; A61K 31/70
[52] U.S. Cl. ........................... 514/49; 514/50; 536/231
[58] Field of Search .................. 536/23; 514/49, 50

[56] References Cited

U.S. PATENT DOCUMENTS

| | | | |
|---|---|---|---|
| 3,870,700 | 3/1975 | Kotic et al. | 536/23 |
| 4,210,638 | 7/1980 | Greer | 514/50 |
| 4,434,788 | 3/1984 | Nakotsugawa | 514/50 |

FOREIGN PATENT DOCUMENTS

| | | | |
|---|---|---|---|
| 0045944 | 2/1982 | European Pat. Off. | 514/50 |
| 77233 | 10/1970 | Fed. Rep. of Germany | 536/23 |
| 0151987 | 11/1979 | Japan | 514/50 |

OTHER PUBLICATIONS

Mitchell et al., Int. J. Radiation Oncology Biol. Phys. 12, pp. 1513–1518, (1986).
Santos et al., Chemical Modifiers of Cancer Treatment Conference, in Paris, France, Mar. 21–25, 1988.
Martinez et al., Int. J. Radiation Oncology Biol. Phys. 11, pp. 123–128, (1985).
Jackson et al., Am. J. Clin. Oncol., 10(5), pp. 437–443, (1987).
Russo et al., Cancer Research 44, pp. 1702–1705, (1984).
Kinsella et al., Int. J. Radiation Oncology Biol. Phys. 10, No. 1, pp. 69–76, (1984); 10, No. 8, pp. 1399–1406, (1984); 13, No. 5, pp. 733–739, (1987).
Giusti et al., Enzym. Biol. Clin. 11, pp. 375–383, (1970).
Phuphanich et al., Int. J. Radiation Oncology Biol. Phy., vol. 10, pp. 1769–1772, (1984).
Kinsella et al., Cancer, Mar. 1, pp. 908–915, (1987).
Szybaski et al., Cancer Chemotherapy Report, Part 1, vol. 58, No. 4, pp. 539–557, (1974).
Brown et al., Chemical Abstracts, vol. 75, 1971, 95151k.
Altman et al., Chemical Abstracts, vol. 66, 1967, 72969h.
Chang et al., Chemical Abstracts, vol. 98, 1983, 191297h.
Tsuneo et al., Chemical Abstracts, vol. 74, 1971, 28490m.
Yoshida et al., Chemical Abstracts, vol. 96, 1982, 210557n.
Kreis et al., Helv. Chem. Acta, 61, (1978), pp. 1011–1016.

(List continued on next page.)

Primary Examiner—Herbert J. Lilling
Attorney, Agent, or Firm—Armstrong, Nikaido, Marmelstein, Kubovcik & Murray

[57] ABSTRACT

Tumors are sensitized to radiation by administration of 5-chlorodeoxycytidine (5-CldC) or 5-halo-2'-halo-2'-deoxy-cytidine or -uridine derivatives. Tetrahydrouridane (H₄U) and/or 2'-deoxytetrahydrouridine (dH₄U) is preferably coadministered with the deoxycytidine derivative to inhibit deamination of the deoxycytidine derivatives. Optional pre- or concurrent treatment with agents to reduce the amount of competing metabolites to favor CldC, such as 5-fluorodeoxyuridine, results in a procedure that significantly increases the dose effects of X-radiation. Pharmaceutical compositions suitable for the sensitization of tumors to radiation are also disclosed.

11 Claims, 7 Drawing Sheets

OTHER PUBLICATIONS

Mekras et al., Chemical Abstracts, vol. 101, 1984, 65639p.

Perez et al., Chemical Abstracts, vol. 101, 1984, 225942n.

Perez et al., "Marked Radiosensitization of Cells in Culture to X Ray by 5-Chlorodeoxycytidine Coadministered with Tetrahydrouridine, and Inhibitors of Pyrimidine Biosynthesis", Int. J. Radiation Oncology Bio. Phys. vol. 1, pp. 1453-1458.

Perez et al., "Sensitization to X Ray by 5-Chloro-2'-deoxycytidine Co—administered with Tetrahydrouridine in Several Mammalian Cell Lines and Studies of 2'-Chloro Derivatives", Int. J. Radiation Oncology Biol. Phys., vol. 12, pp. 1523, 1527.

Russell et al., "In Vitro and in Vivo Radiation Sensitization by the Halogenated . . . ", Cancer Research, vol. 46, pp. 2883-2887, Jun. 1986.

Mekras et al., "Use of 5-Fluorodeoxycytidine and Tetrahydrouridine to Exploit High Levels of Deoxycytidylate Deaminase in Tumors to Achieve DNA—and . . . , Cancer Research", vol. 44, pp. 2551-2560, Jun. 1984.

Santos et al., "Radiation, Pool Size and Incorporation Studies with the Potential Selective Radiosensitizer, 5-Chloro-2'-Deoxycytidine in Mice," University of Miami, School of Medicine, Miami, Fla. 33101 USA.

Ellims et al., "Deoxycytidylate Deaminase Activity in Lymphoproliferative Disorders", Monash University Department of Medicine, Alfred Hospital, Prahran, 3181, Victoria, Australia and Division of Anatomical Patholyg, Prince Henry's Hospital, St. Kilda Rd., Melbourne, 3004, Victoria Australia, Feb. 2, 1983.

| CONDITION | % VIABILITY OF UNIRRADIATED CELLS |
|---|---|
| ● MEM + H₄U | |
| ▲ CldC 0.1 mM + H₄U 4 mM | 85 |
| ○ METHOTREXATE 0.005 µg/ml + H₄U | 92 |
| ■ METHOTREXATE + CldC + H₄U | 66 |

| ● MEM | | | | |
|---|---|---|---|---|
| PALA mg/ml | FdU μM | CldC mM | H4U mM | % VIABILITY UNIRRADIATED CELLS |
| ○ 0.2 (18)* | 0.1 (6) | 0.6 (56) | 0.4 | 2.7 |
| □ 0.2 (18) | 0.1, 0.02 (6), (56) | 0.6 (56) | 0.4 | 1.8 |
| ■ 0.2 (18) | 0.1 (6) | 0.2 (56) | 0.4 | 12 |
| △ 0.2 (18) | 0.1, 0.02 (6), (56) | 0.2 (56) | 0.4 | 3.8 |

*(HOURS)

● MEM

| PALA mg/ml | FdU μM | CldC mM | H4U mM | % VIABILITY OF UNIRRADIATED CELLS |
|---|---|---|---|---|
| ■ 0.2 * (20) | 0.1 (5) | 0.2 (64) | 0.4 | 9.8 |
| □ 0.2 (20) | 0.1 (5) | 0.1 (64) | 0.4 | 9.3 |
| △ 0.2 (21) | 0.1 | 0.2 (57) | 0.4 | 1.6 |

*(HOURS)

| CONDITION | % VIABILITY OF UNIRRADIATED CELLS |
|---|---|
| ● MEM | |
| ○ dH₄U | 80 |
| □ CldC 0.1 mM + dH₄U 4 mM | 49 |

| CONDITION | % VIABILITY OF UNIRRADIATED CELLS |
|---|---|
| MEM | |
| dH₄U 6mM | 85 |
| DEAZAURIDINE 12 μM + dH₄U | 64 |
| CldC 0.6 mM + dH₄U | 18 |
| CldC + dH₄U + DEAZAURIDINE | 21 |

| CONDITIONS | %S FOR UNIRRADIATED CELLS |
|---|---|
| ● MEM | |
| △ { PALA (0.2) 18h FdC (0.02) & H₄U (25) 5h<br>mg/ml    μM              μg/ml<br>CldC (.2) & H₄U 68h<br>mM } | 20 | h: (HOURS)

● MEM

| PALA mg/ml | FdU μM | FdC & H4U μM μg/ml | CldC & H4U mM μg/ml | %S FOR UNIRRADIATED CELLS |
|---|---|---|---|---|
| ○ 0.1 (20)* | .02 (7) | - | 0.1   25 (63) | 14 |
| ■ 0.2 (20) | 0.02 (7) | - | 0.2   25 (63) | 6.7 |
| □ 0.1 (20) | - | 0.02   25 (7) | 0.2   25 (63) | 15 |
| ▲ 0.2 (20) | 0.02 (7) | - | 0.1   25 (63) | 19 |
| △ 0.1 (20) | 0.02 (7) | - | 0.2   25 (63) | 8.4 |

*(HOURS)

METHOD AND MATERIALS FOR SENSITIZING NEOPLASTIC TISSUE TO RADIATION

CROSS REFERENCE TO RELATED APPLICATION

This application is a continuation-in-part of U.S. application Ser. No. 545,693 filed Oct. 26, 1983, now abandoned.

BACKGROUND OF THE INVENTION

The present invention pertains to combination radiotherapy of tumors and more specifically to pharmaceutical compositions and methods of treatment and therapy designed to sensitize tumors in animals, notably humans, and render them more sensitive to radiation, thus significantly reducing the amount of radiation required to kill neoplastic cells while at the same time making the radiation far more tissue specific to the tumor site.

More conventional radiation sensitizers are hypoxic cell sensitizers such as the antifilarial agent, misonidazole, which causes the complexities of neurotoxicity when it is utilized in humans. The 5-halogenated pyrimidine analogs are very distinct agents from the hypoxic cell sensitizers, for they have a completely different mode of action. We have found that cultured mammalian cells, when exposed to bromo-2'-deoxyuridine (BrdU) or other halogenated analogs of thymidine incorporate the compound into DNA resulting in sensitization of these cells to X-irradiation. Rapid catabolism or degradation of BrdU has limited its clinical effectiveness for the sensitization of rapidly growing neoplasias.

We have determined that 5-chloro-2'-deoxycytidine (CldC), which is not readily degraded due to the 4-amino group that protects the compound from catabolism by nucleoside phosphorylases, is anabolized by a different set of enzymes than the corresponding dU analog. In addition CldC is less cytotoxic than CldU. An object of the present invention is to define a class of stable, selective cell sensitizers that are not easily catabolized against tumors, both rapidly and moderately growing and malignant, and that will allow the X-ray therapist to focus the X-ray beam (or other source of radiation) on the tumor tissue site using significantly less, say one-fourth, of the dose of radiation otherwise required to achieve the same extent of tumor kill without damage to the underlying tissue. Expressed in another way, the radiotherapist is able to more aggressively kill neoplastic tissue while causing no more damage to normal tissue using the procedures and materials of the present invention than with conventional modalities of irradiation.

Thus an object of the present invention is to provide therapeutic materials and procedures for treating skin lesions using, for instance, ultraviolet light, near visible light (313 nm), and for solid tumors: X- or gamma ray, beta, neutron and other radiation entities.

Another object of the invention is to sensitize possible sites of metastic invasion to radiation, particularly X-ray, using the disclosed materials and procedures.

Should the patient develop toxicity from the mildly aggressive therapy employed, particularly with the pretreatment with FdU and PALA either before or with the sensitizing composition, thymidine or deoxycytidine, two non-toxic metabolites, may be provided the patient at the conclusion of radiation therapy. These serve to mitigate the untoward effects, if any, of the drug therapy by antagonizing or reversing any toxic effects of the chemotherapeutic agents employed.

The method of the present invention may be used primarily with x-ray or gamma (derived from cobalt, for example) radiation. We also consider the procedure to be effective with the use of ultraviolet light, near visible light (313 nm) for skin lesions and for beta, neutron and other radiation entities. The molecular basis of sensitization has been clearly established for ultraviolet light (260 nm) and near visible light (313 nm) (both nonpenetrating) and for X- or gamma-radiation.

SUMMARY OF THE INVENTION

According to one aspect, patients having tumors requiring radiation therapy are administered, preferably on a slow release basis, 5-chloro-2-deoxycytidine and-/or 5-chloro 2'-halo-2'-deoxycytidine, wherein halo is fluoro, chloro, bromo or iodo, preferably chloro. The deoxycytidine compound is preferably administered with a deamination inhibitor, preferably tetrahydrouridine ($H_4U$) and/or 2'-deoxytetrahydrouridine ($dH_4U$) for a period of time until amounts sufficient to sensitize the tumor tissue to radiation are present in the tumor tissue. Optimally, the patient is given a pretreatment regimen designed to lower the metabolites competing for CldC, or a special limited diet is used for the same purpose. Drug treatment is suspended and radiation therapy initiated at the dosage required to kill the exposed tumor tissue while avoiding or reducing significant damage to the underlying tissue. If toxicity is encountered in the pretreatment sensitization procedure, thymidine or deoxycytidine may be administered to the patient immediately following the radiation treatment to counteract toxicity without affecting selective tumor kill.

Pharmaceutical compositions providing the required amounts of 5Cl-2'-halo-2'-dC or of 5halo-2'-halo-2'-dU, as well as compositions providing the required amounts of 5-CldC and $H_4U$ or $dH_4U$ in pharmaceutically acceptable formulations are also described.

According to another aspect, patients are administered with a 5-chloro,5-bromo or 5-iodo-2'-halo-2'-deoxyuridine compound, preferably the 5-bromo or 5-iodo compound, wherein halo is fluoro, chloro, bromo or iodo, preferably chloro. In this instance, because of the deoxyuridine moiety does not contain an amino substituent, it is not necessary to inhibit deamination thereof (this is discussed in more detail below), and so administration of $H_4U$ and/or $dH_4U$ with the deoxyuridine compound is not required.

BRIEF DESCRIPTION OF THE DRAWINGS

FIGS. 1–7 are graphs wherein the log of the fraction of treated or untreated HEp-2 cells surviving is plotted against to the amount of radiation in rads to which those cells had been subjected. FIGS. 1A–7A are legends corresponding to FIGS. 1–7, showing the conditions of treatment of the HEp-2 cells (and the viability of unirradiated cells) as more fully described under Examples of the Invention.

DETAILED DESCRIPTION OF THE INVENTION

Figures 1, 1A:
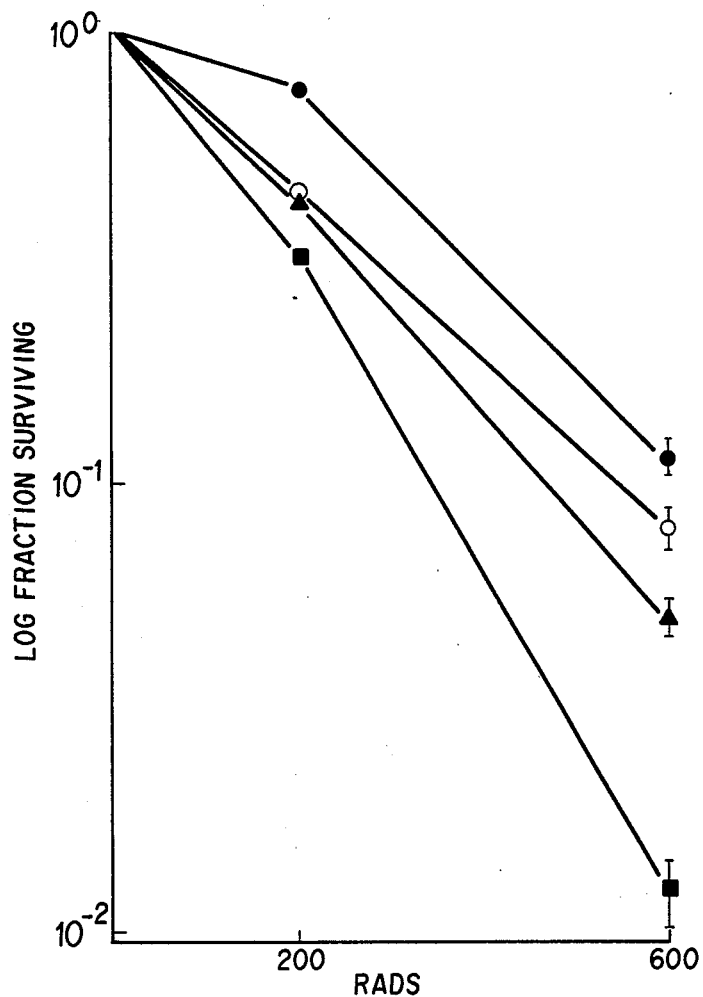

Rapid catabolism and generalized toxicity have limited the use of 5-halogenated analogs of deoxyuridine as tumor sensitizers. In one approach to this problem, 5-halogenated analogs of deoxycytidine (dC) or of 2'- halo-2'-deoxycytidine were utilized, which are not catabolized unless they are deaminated. To prevent deamination by cytidine deaminase (CD), which is extremely active in human serum, it is preferred, according to the invention, to administer tetrahydrouridine (H4U), a potent inhibitor of this enzyme, either concurrently with, or at about the same time as, administration of the deoxycytidine compound.

Our previous enzyme kinetic studies with 5-bromo-2'-deoxycytidine (BrdC) and 5-iodo-2'-deoxycytidine (IdC) indicate that they would not be suitable, in this approach to circumvent catabolism, because they are poor substrates for deoxycytidine kinase. Unlike BrdC, chlorodeoxycytidine (CldC) does not require deamination at the nucleoside level for its anabolism because it possesses a reasonable Km value (56 μM) with respect to mammalian deoxycytidine kinase compared to 400 μM for BrdC and 2 μM for dC. Studies with HEp-2 cells suggest that CldC (+H4U) is metabolized as follows:

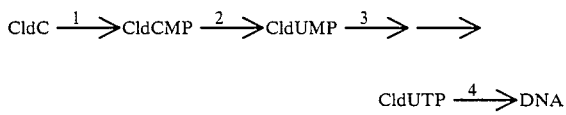

(1=deoxycytidine kinase, 2=deoxycytidylate deaminase (dCMPD), 3-thymidylate kinase, 4-DNA polymerase). These four enzymes are elevated in many human tumors. For example, dCMPD activity in human malignant tumors is 20–80 fold higher than that of normal tissue.

In X-radiation studies with HEp-2 cells, we have obtained 3.4–3.7-fold dose increase effects. Cells were preincubated with inhibitors of de novo pyrimidine synthesis: N-(Phosphonacetyl)-L-aspartate (PALA) and 5-fluorodeoxyuridine (FdU) for 20 hours and 5 hours, respectively and then incubated in the presence of 0.1 or 0.2 mM CldC and H4U (100 μM) for 64 hours. These conditions result in 40–50% substitution of CldU for thymidine in DNA. Viabilities of 10% ±4 to 12% ±5 were obtained for drug-treated unirradiated cells. Inhibitors of thymidylate synthesis that are more DNA and tumor selective than FdU are also within the ambit of this invention. CldC and its metabolites are not toxic unless deamination occurs. CldC should be converted preferentially to CldUMP in tumors possessing high levels of dCMPD and then be further anabolized to CldUTP, resulting not only in radiosensitization but also in selective tumor toxicity, presumably as a result of inhibition of ribonucleoside diphosphate reductase by CldUTP.

Addition of dH4U, which results in inhibition of CD and dCMPD, has enabled us to study radiosensitization due to incorporation of CldC as such into DNA. However, as noted above, it is not necessary to use dH4U (or H4U) with the 5-iodo or 5-bromo 2'-halo- dU derivatives since deamination is not a problem in those derivatives.

The preferred materials used to carry out the present invention, including abbreviations and structural formulae, are listed in Table I below. 5-chlorodeoxycytidine (CldC) was obtained from Calbiochem-Behring and has been described in the literature as an antiviral (antiherpetic); see Fox, Mekras, Bagwell and Greer et al, Capacity of Deoxycytidine to Selectively Anatgonize Cytotoxcicity of 5-Halogenated Analogs of Deoxycytidine Without Loss of Antiherpetic Activity, Antimicrob. Agents Chemother., Vol. 22, No. 3, p. 431–441 (Sept. 1982). Additionally DeClercq et al used CldC in cell cultural studies (no indication is given for use in cancer therapy) the data indicating CldC was unremarkable in the system employed; see "Role of Deoxycytidine Kinase in the Inhibiting Activity of 5-substituted 2'-Deoxycytidines and Cytosine Arabinosides on Tumor Cell Growth", J. Balzarini, and De Clercq, Erik, Molecular Pharmacology, Vo. 23, p. 175–181 (1982).

The 5-chloro-2'-halo-2'-deoxycytidines as well as the 5-chloro, 5-bromo or 5-iodo-2'-halo-2'-deoxyuridine derivatives may be prepared according to the procedure described by Codington, Doerr and Fox, Nucleosides, XVIII Synthesis of 2'-Fluorothymidine, 2'-Fluorodeoxyuridine, and other 2'halogeno-2'-deoxy Nucleosides, J. Org. Chem., 29, 558 (1964).

Tetrahydrouridine (H4U) was obtained as a gift from the Drug Development Branch of the National Cancer Institute, Bethesda, Maryland, its synthesis is described by Hanze, Catalytic Reduction of Pyrimidine Nucleosides, J. Amer. Chem. Soc. 89 6720–6725 (1967). 2'-deoxytetrahydrouridine (dH4U) inhibits cytidine deaminase and when phosphorylated it also inhibits deoxycytidylate deaminase. The synthesis of H4U and dH4H are described in U.S. Pat. No. 4,017,606 (Hanze et al). To our knowledge dH4U has never been utilized in tumor therapy with an analog of deoxycytidine.

5-fluorodeoxyuridine (FdU) is a known antitumor agent available from Sigma Chemical Company, 5-fluorodeoxycytidine (FdC), which has a greater. selectivity against tumors, may also be used. FdC, not previously been used for tumor radiosensitization, may be prepared according to Fox, J. J., Wempen, I., and Duschinsky, R., Nucleosides of 5-Fluorocytosine. Proc. of the 4th International Congress of Biochemistry 15 p. 6 (1958). For the procedure of the present invention it is coadministered with tetrahydrouridine.

N-(Phosphonacetyl)-L-aspartate (PALA) has been used alone and with 5-flururoruracil (5-FUra) as an antitumor agent but not to pretreat tumor cells in conjunction with radiation. PALA was obtained from the Drug Development Branch of the National Cancer Institute at Bethesda, Maryland.

The strategy of pretreatment is to inhibit the de novo pathway of pyrimidine biosynthesis.

The use of 5-trifluoromethyl-2'-deoxycytidine (F3 methyldC) together with tetrahydrouridine (H4U) in the treatment of Herpes or Herpes-like viruses is described in U.S. Pat. No. 4,210,638 to Sheldon Greer.

TABLE I

| Name | Abbreviation | Structure |
|---|---|---|
| tetrahydrouridine | H₄U | 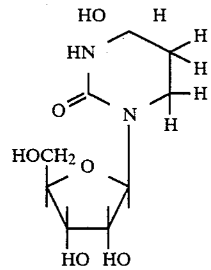 |
| 2'-deoxytetrahydrouridine | dH₄U | 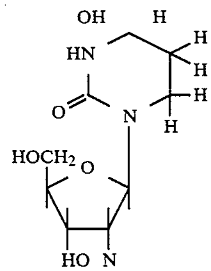 |
| 5-chloro-2'-deoxycytidine | 5-CldC | 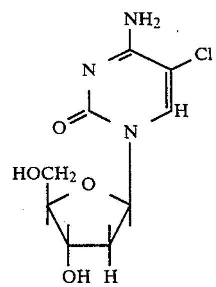 |
| 5-fluoro-2'-deoxyuridine | FdU | 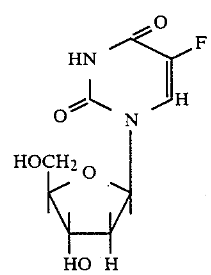 |
| 5-fluoro-2'-deoxycytidine | FdC | 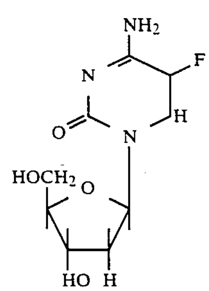 |
| N—(Phosphonacetyl)-L-aspartate | PALA | 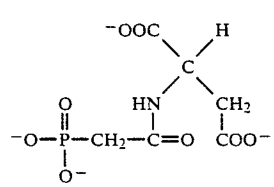 |

The abbreviations used include: CD, cytidine-deoxycytidine deaminase; CHO, Chinese hamster ovary cells; CldC, 5-chloro-2'deoxycytidine; CldCMP, 5-chloro-2'-deoxycytidine-5'-monophosphate; CldUMP, 5-chloro-2'deoxyuridine-5'-monophosphate; dC, deoxycytidine; dCK, deoxycytidine kinase; dCMPD, deoxycytidylate deaminase; $dH_4U$, 2'deoxytetrahydrouridine; dT, thymidine; dU, 2'-deoxyuridine; dUMP, 2'-deoxyuridine-5'monophosphate; FdC, 5-fluoro-2'-deoxycytidine; FdU, 5-fluoro-2'deoxyuridine; FdUMP, 5-fluoro-2'-deoxyuridine-5'-monophosphate; $F_3$methyldC, 5-trifluoromethyl-2'-deoxycytidine; FUra, 5-fluorouracil, HEp-2, human epidermoid laryngeal carcinoma cells, $H_4U$, tetrahydrouridine; TK, thymidine kinase; TS, thymidylate synthetase; TTP, thymidine-5'-triphosphate.

While not wishing to be bound by any theory, we offer the following as a further explanation of the possible mode of action of CldC as a radiosensitizing agent when coadministered with $H_4U$ as well as with $dH_4U$. With a low concentration of tetrahydrouridine to protect the nucleoside analogs from systemic catabolism, one may envision that BrdC and IdC as well as CldC will act as selective radiosensitizers against tumors with high levels of cytidine deaminase. At higher concentrations of $H_4U$, CldC should be converted preferentially at the tumor site to CldUMP in human tumors possessing high levels of deoxycytidine kinase and dCMP deaminase. When anabolized to CldUTP not only will there be selective tumor toxicity because of inhibition of ribonucleoside reductase by CldUTP, but in addition the incorporation of CldU into DNA will lead to tumor radiosensitization. Selectively will result not only because of accelerated DNA synthesis, but because of elevation of key enzymes in the tumor that are critical for this strategy: in addition, there will be the customary selectivity that is associated with utilizing a focussed beam of irradiation overlaying the tumor. This approach is amenable to rescue with deoxycytidine and thymidine immediately after irradiation. A typical irradiation experiment in the mouse would involve an i.p. injection of CldC+$H_4U$ every 8 to 10 hrs in a 30 to 36 period, for example. The goal is to obtain substantial incorporation of CldC into both strands of DNA. The use of $dH_4U$ may result in the incorporation of CldC as such into the DNA cells. However, in this case there may be less selectivity against the tumor for we are probably only exploiting the elevation of dC kinase that occurs in tumors.

EXAMPLES OF THE INVENTION

To determine whether 5-chlorodeoxycytidine (CldC) and tetrahydrouridine ($H_4U$) has potential as a radiosensitizing combination, we tested these agents in HEp-2 cells. These cells were chosen as our model system since they possess elevated levels of activity of deoxycytidine kinase (dCK), cytidine deaminase (CD) and deoxycytidylate deaminase (dCMPD); the enzymatic profile necessary for metabolic conversion of CldC to an established radiosensitizer, CldUTP. TMP kinase and DNA polymerase are also elevated in tumors; these elevations should assure further preferential incorporation of CldU into tumor DNA.

Many of the experiments described below were done utilizing only one dose of radiation (usually 500 or 600 rads). Although one can not accurately calculate dose-increase effects based on such limited data, we have nonetheless pursued our studies in this manner in order to test many different combinations of metabolites and antimetabolites in the same experiment. Naturally, we are missing important features seen only at low doses. However, this approach fulfilled the need to search and find optimal regimes. We have found that sensitization effects are more pronounced at doses of 500 or 600 rads. Preliminary experiments that demonstrate some of the sensitization effects that have been obtained are described below.

CldC (and $H_4U$), our storage and DNA- and target-directed form of CldU, coadministered with methotrexate gave an enhancement ratio of 2.0-fold. This is illustrated in FIG. 1. This effect was obtained with a viability of 66%.

In the next series of experiments, cells were pretreated prior to CldC+$H_4U$ administration with the inhibitor of de novo pyrimidine biosynthesis, N-(Phosphonacetyl)-L-aspartate (PALA). PALA is a potent inhibitor of aspartate transcarbamylase and causes a depletion of intracellular pyrimidine pools. Liang et al found that PALA and fluorouracil (FUra) were synergistic when PALA was administered prior to FUra. These investigators speculated that the reason for this synergistic interaction was due to marked decreases in dUMP pools in cells preincubated with PALA. Decreased dUMP pools should help potentiate FdUMP inhibition of thymidylate synthetase leading to decreased levels of TTP; which would then result in less competition for the incorporation of CldU into DNA and greater activity of dCMPD. This is the rationale for the use of the combination of PALA and FdU in radiation experiments. Furthermore, PALA, by reducing intracellular pyrimidine biosynthesis may lower competing substrates for the activation of CldC to CldUTP.

Figures 2, 2A:
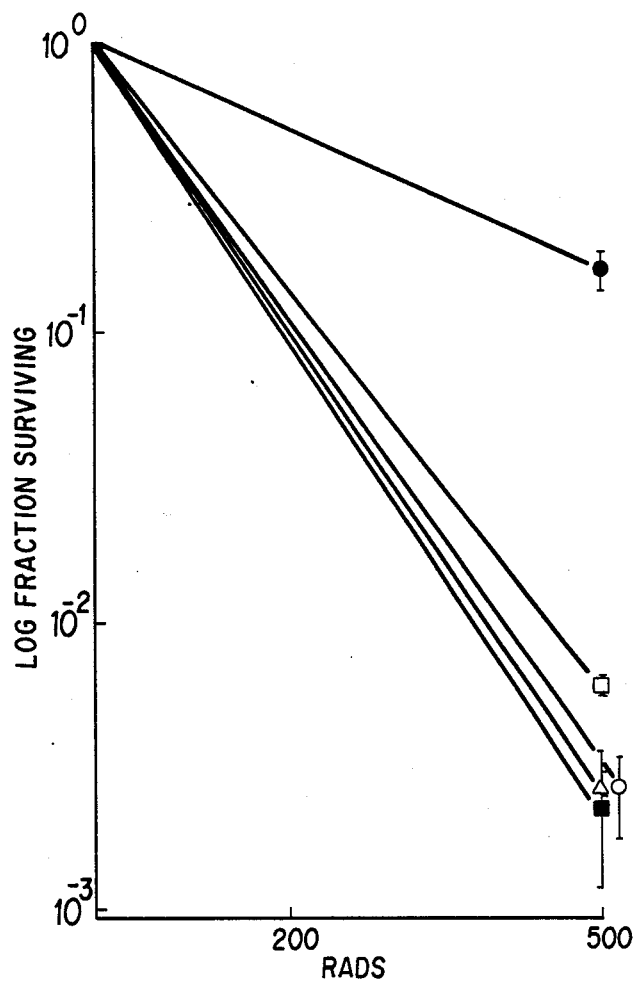

In recent experiments PALA has been administered 12–20 hours prior to FdU pretreatment, which is for 6 hours. Evans et al have shown that FdUMP pools persist after FdU or FUra administration. Coexposure of HEp-2 cells to CldC+$H_4U$ and FdU for 48 hours in comparison to pretreatment with FdU for 6 hours does not lead to a greater enhancement of radiosensitization by CldC 30 $H_4U$ but only results in greater cytotoxicity. Following the pretreatment schedule described above, we have been able to lower the concentration of CldC (from 0.6 mM to 0.2 mM) and achieve better sensitization to X-ray. These results are illustrated in FIG. 2. CldC at 0.2 mM gives a dose increase effect of 3.6 with an associated 12.4% ±5.1% (±S.E.) viability, whereas CldC at a concentration of 0.6 mM results in a 3.0-fold dose increase.

Figures 3, 3A:
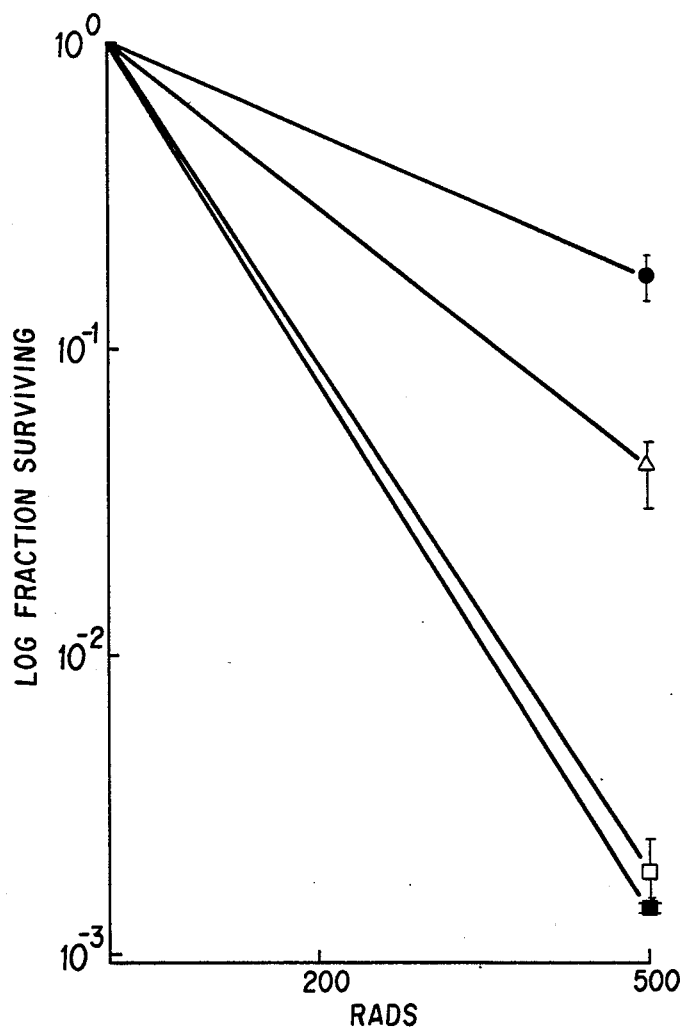

In the experiment summarized in FIG. 3 we attempted to lower the concentration of CldC further, but lost sensitization at a concentration of 0.05 mM. In an effort to minimize the number of manipulations performed, cells were exposed to PALA and FdU for 21 hours as a single pretreatment, but this resulted in a significant loss in viability (viability equals 1.6%) with no gain in radiosensitization (a 1.9 dose-increase). A 3.8-fold dose-increase effect was achieved with conditions similar to those of the previous experiment with 9.8%±4.0% (±S.E.) viability.

The rationale for utilizing PALA and FdU pretreatment is to achieve greater radiosensitization with CldC+$H_4U$; however our approach is strengthened by the fact that PALA and fluorinated pyrimidines are agents which are effective in combination chemotherapy. The conversion of CldCMP to CldUMP at the tumor site because of elevated levels of dCMP deaminase, is an example of tumor-directed toxicity as is the case with FdC. The target enzyme in CldC therapy is presumably nucleoside diphosphate reductase, which is likely inhibited by CldUTP. FdC pretreatment rather than FdU is currently believed to achieve a greater measure of tumor- and DNA-directed toxicity with no loss of radiosensitization with CldC, $H_4U$ and PALA in animal systems.

Figures 4, 4A:
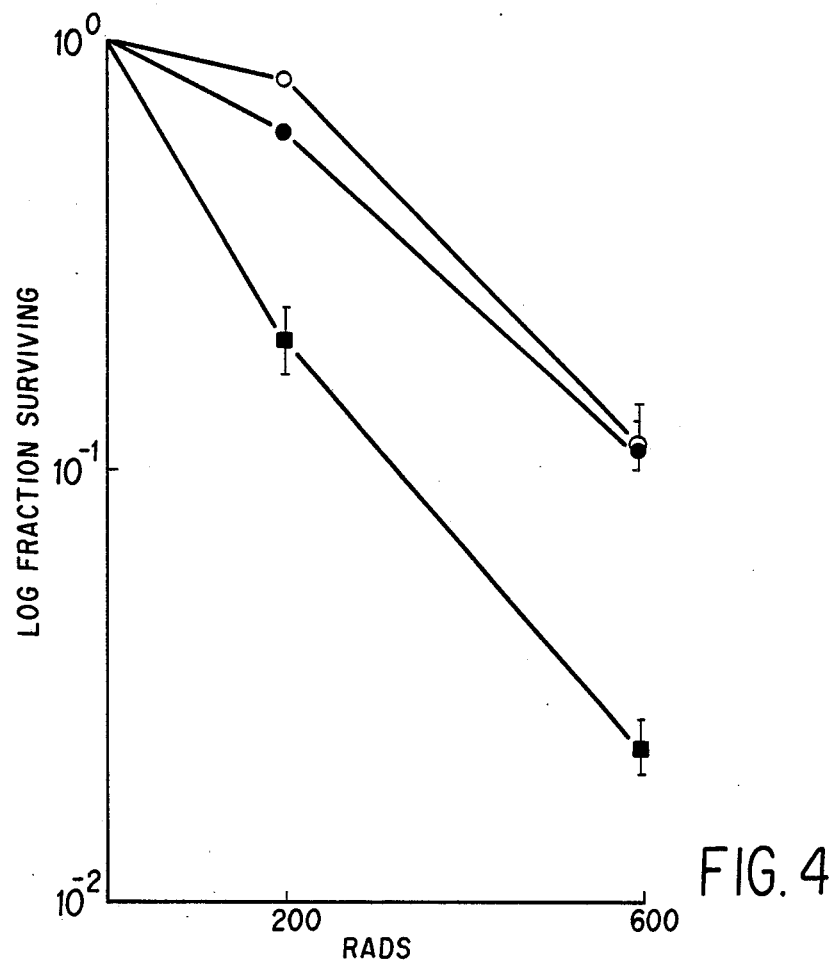

The experiment summarized in FIG. 4 illustrates our second approach with CldC; that is, to examine the radiation effects resulting from the incorporation of CldC as such (without prior deamination of CldU) in DNA. This may be accomplished by $dH_4U$, which as $dH_4UMP$ inhibits both deoxycytidine and deoxycytidylate deaminases. If both sites of deamination are blocked, the only anabolic route for CldCMP will be to become phosphorylated further to CldCTP. In this initial experiment a 1.8-fold dose-increase effect was obtained with CldC and $dH_4U$.

Figures 5, 5A:
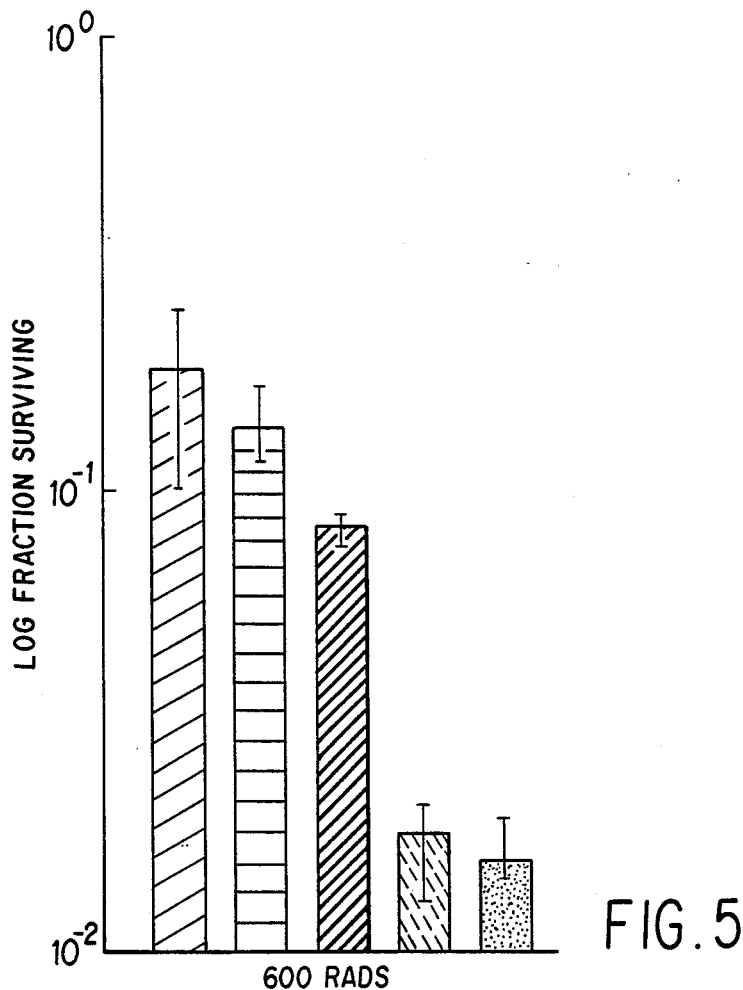

In subsequent experiments we sought to lower competing dCTP pools by utilizing 3-deazauridine. Deazauridine is a potent inhibitor of CTP synthetase and did not appear to enhance sensitization in this experiment. In the bar graph depicted in FIG. 5 a 2.0-fold dose-increase effect was obtained by CldC, $dH_4U$ and deazauridine with 21% viability.

It should be noted that the most striking effects we have obtained have been with the use of CldC and $H_4U$ rather than with CldC+$dH_4U$. That is, the combination of CldC+$H_4$has resulted in a 3.4 to 3.8 dose enhancement effect with appropriate pretreatment (PALA and an F-pyrimidine analog).

Figures 6, 6A:
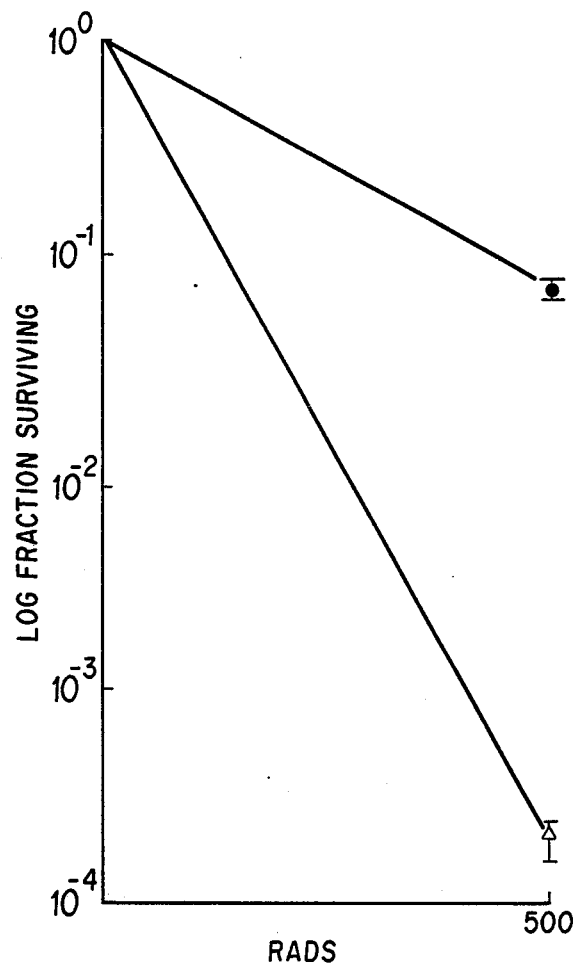

FIG. 6 summarises an experiment in which a 3.4 dose enhancement effect is displayed when FdC+$H_4U$ replaces FdU in the pretreatment procedure prior to the addition of CldC and $H_4U$. 5-fluorodeoxycytidine+tetrahydrouridine should result in tumor directed toxicity; that is, it should be more tumor specific than FdU. Thus FdC+$H_4U$ may be used to obtain greater efficacy without loss of radiosensitization.

Figures 7, 7A:
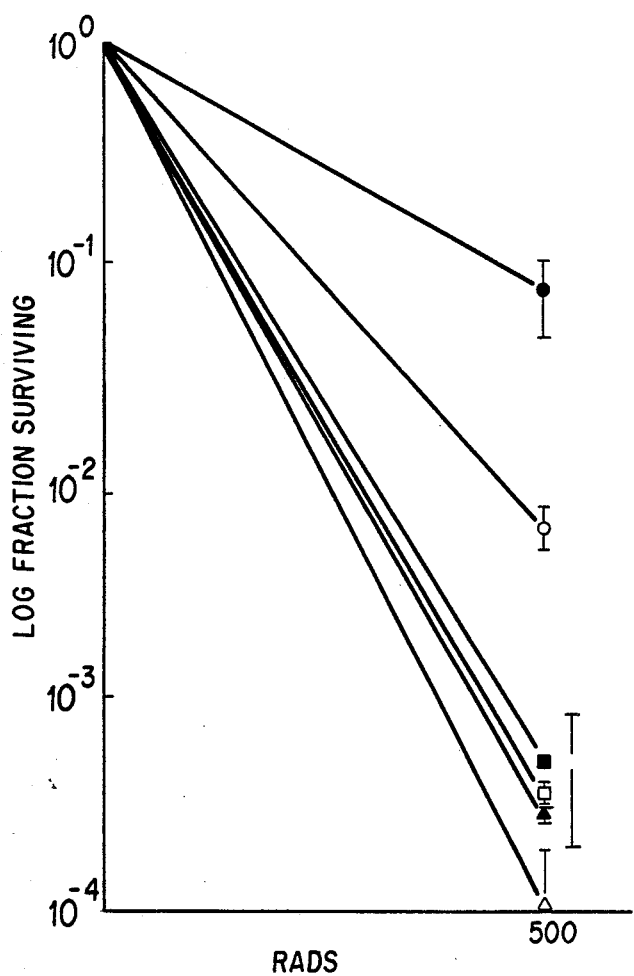

FIG. 7 summarizes an experiment in which we have demonstrated that lowering both PALA and CldC concentrations results in significant loss of radiosensitization without a substantial decrease in toxicity. FdU and FdC+$H_4U$ pretreatment are essentially equivalent in terms of effective CldC ratiosensitization, with FdC+$H_4U$ displaying less toxicity, which is desirable. A maximum 3.4 to 3.6 dose enhancement effect was displayed in this experiment.

BrdU has been shown under the most optimal conditions in cell culture to display a 3.5 to 4.0 dose-increase effect with X-ray and with ultraviolet light. We have now achieved comparable results with a combination of agents that will lead to the circumvention of catabolism and to tumor selectivity—two features not readily achieved with BrdU. Most importantly, with this method one may irradiate a tumor at ¼ the dose to prevent damage to underlying tissue or to more aggressively irradiate a tumor without an increase in damage to normal tissue.

Pharmaceutical Presentation—pharmaceutical compositions comprising, as the active ingredient(s), radiation-sensitizing effective amounts of 5-CldC and $H_4U$ and/or $dH_4U$ together with a pharmaceutically acceptable carrier or diluent, for intraperitoneal administration for animal studies, intraveneous, subcutaneous, intramuscular, oral or topical administration are included in the present invention. While the components of the composition may be administered separately, it is preferred to coadminister them as a mixture. The concentration of each of the active ingredients may vary from about 0.01 to about 25% by weight depending on the route of administration, the frequency of administration, the severity of the condition, the age, weight and general physical condition of the patient being treated as well as the size and location of the tumor to be irradiated. Alternatively a more concentrated solution will be used, e.g. 75g/100 ml, or a slow i.v. infusion of a 0.1 to 25% (or higher) concentration will be used. When the composition is in the form suitable for topical administration, for example a cream, the concentration of the total of 5-CldC and $H_4U$ or $dH_4U$ will generally vary from about 5 to 50 weight %, preferably about 5 to 20 wt. %, more preferably from about 5 to 10 wt. %. When the composition is in the form suitable for intraperitoneal administration for animal studies, for example, an aqueous solution of CldC and $H_4U$ or $dH_4U$ the concentration will generally vary from about 0.5 to 5% w/v, more usually from 1% w/v. For oral administration, the concentration will generally be from 0.05 to 10 wt. %, preferably about 0.5 to 5 wt. %, and more preferably about 1 to 2 wt. %.

When used for intraveneous injection, the concentration of the active components will vary from about 0.05 to about 5% w/v, preferably about 0.1 to about 0.5% w/v. For intramuscular injection, the same concentrations as described above for the intraperitoneal mode of administration will be utilized.

Other means of administration may also be used. Suppositories may be used for sustained release purposes. Slow-release surgical implants are also envisaged.

The pharmaceutically acceptable carriers or diluents employed in the compositions of the present invention may be any compatible non-toxic material suited for mixing with the active compounds. When the composition is in a form suitable for parenteral use, for example intramuscularly or intravenously, the carrier which preferably is an aqueous vehicle, may also contain other conventional additives, such as a suspending agent for example methyl cellulose or polyvinylpyrrolidone (PVP), and a conventional surfactant. For oral administration, the compositions can be formulated as aqueous solutions, suspensions, capsules or tablets, suitably containing appropriate carriers or diluents, for example lactose, starch and/or magnesium stearate for flavoring agents, syrups, sweeteners or coloring materials as customarily used in such preparations.

A preferred pharmaceutical composition provides the patient with a total i.v. dosage of from 3 to 5 ml (cc) per dosage calculated on 70 kg body weight of the patient.

Clinical Protocol: The patient will be given drugs i.v. or i.m. or in an oral or suppository form or in a slow release form. A slow release administration of CldC and tetrahydrouridine may be particularly advantageous. Different routes may be used for individual drugs in one treatment protocol.

PALA in 10 ml ampules containing PALA disodium (1.0 gram) with Edetate disodium (1 mg) and NaOH to adjust pH to 6.5 to 7.5 will be given to a cancer patient with a solid tumor at a range 2 mg to 300 mg/kg per dose preferably 5 to 20 mg/kg per dose and more likely 10 mg/kg per dose. Twelve to thirty six hrs later preferably 18 to 26 and most likely 24 hrs later, FdU at a concentration of 10–75 mg/kg per dose, preferably 25 to 60 more likely 50 mg/kg would be administered. Alternatively FdC at a similar concentration range as FdU will be administered but in this case it will be coadministered with tetrahydrouridine at a concentration range from 10 to 200 mg/kg preferably 15 to 100 and more likely 25 mg/kg. The ratio of $H_4U$ to FdC will range from 4:1 to 0.2:1 preferably 1.5:1 to 0.75:1 more likely 1:1.

Three to 12 hrs later preferably 4 to 8 hrs, more likely 6 hrs later the series of administration of 5-CldC and $H_4U$ will begin.

The dose of 5-CldC will range from 200 to 2500 mg/kg per dose, preferably 500 to 2000 mg/kg, more likely 1500 mg/kg.

The dose of $H_4U$ will be the same as that given with FdC described above. The ratios are, however, different; namely, the ratio of $H_4U$ to CldC will range from 1:30 to 1:5, more usually 1:30 to 1:10 and more likely 1:15.

This will be repeated at 6 to 18 hr intervals more usually 8 to 12 more likely 10 hr intervals. The period of repeated CldC+$H_4U$ administration will be 20 to 60 hrs, more usually 30 to 50 hrs more likely 34 to 48 hrs. Usually CldC+$H_4U$ will be administered in 3 to 4 doses, 8 to 12 hrs apart.

After the last dose of CldC+$H_4U$ an interval of 4 to 18 hrs will ensue prior to irradiation. This period will more preferably be 6 to 14 hrs and more likely 8 to 10 hrs.

The interval between PALA/FdU or FdC antitumor therapy and CldC/$H_4U$ sensitizer therapy, as well as the frequency of administration is determined by the skilled clinician drawing upon previous experiences and observations using this regimen of therapy. The interval between drug therapy and radiation treatment may be varied as well.

The radiation dose, X-ray or gamma-ray, for example, will be either the same or ¼ to ¾ the dose given to the patients not receiving the pretreatment sensitization schedule. This will result in either (a) more aggressive tumor kill without increased damage to underlying tissue when the 4/4 dose is used, or (b) equal tumor kill as that achieved in patients given no treatment but with much less damage to underlying tissues when the ¼ to ¾ doses are used.

If toxicity is encountered due to the drug treatment schedule then thymidine at a dose of 50 to 750 mg/kg, more likely 100 to 500 mg/kg, preferably 200 mg/kg will be given immediately after the radiation treatment. This will be repeated 2 to 3 times at 8 to 12 hr intervals. This treatment is designed to counteract toxicity without adversely affecting selective tumor kill. Deoxycytidine at a concentration range similar to thymidine can be given with or instead of thymidine. When deoxycytidine is administered it will be given at a ratio of tetrahydrouridine to deoxycytidine of 1:0.05 to 1:5.

Deoxycytidine with $H_4U$ or $dH_4U$ may also be given 2–6 hrs after each CldC treatment prior to irradiation.

This course of treatment can be repeated one week to two weeks later and repeated again until the patient receives a total dose of 3000 to 7000 rads. In this strategy, the patient may need less total irradiation to achieve effective tumor kill. This is one advantage of the strategy. The dose of radiation which, in the past provided only partial remission, may result in long term cures. That is the primary advantage of this approach.

The dosages and ranges are summarized in the following table:

TABLE II

| Agent | | DOSAGE* General | Preferred | Most Preferred |
|---|---|---|---|---|
| pretreating | PALA | 2–300 | 5–20 | 10 |
| | FdU or FdC | 10–75 | 25–60 | 50 |
| | +$H_4U$** | 10–200 | 15–100 | 25 |
| Sensitizing | CldC | 200–2500 | 500–2000 | 1500 |
| | $H_4U$ | 10–200 | 15–100 | 25 |
| | $dH_4U$ | 10–200 | 25–125 | 50 |

*expressed in mg/kg body weight/dose
**when FdC is utilized

The above dosages and ranges apply with respect to the 5-chloro-2'-halo-2'-deoxycytidine compounds, as well as the 5-chloro-, 5-bromo- and 5-iodo-2'-halo-2'-deoxyuridine derivatives.

Toxicity Studies: Our analysis of the potential of toxicity using the method herein disclosed indicates that, at most, a 5% weight loss was achieved with no deaths due to toxicity. This is viewed as a trivial and most tolerable weight loss considering the normal aggressive results of the administration of antitumor agents in radiation therapy.

The protocol employed was as follows: Three animals were injected with i.p. with PALA at a dose of 200 mg/kg. This was followed 24 hrs later with an i.p. injection of 5-fluorodeoxyuridine (FdU) at a dose of 50 mg/kg. Four hrs later they were given an i.p. injection of CldC (500 mg/kg) coadministered with 100 mg/kg tetrahydrouridine. The administration of CldC+$H_4U$ at the above indicated concentrations was repeated two more times at ten hour intervals. Only 4% weight loss occurred. No deaths occurred with this protocol.

This protocol was modified using 700 and 1400 mg of CldC/kg and a FdU concentration of 60 mg/kg and extensive incorporation of 5-chlorodeoxyuridine into DNA of tumor tissue was observed.

The procedures of our invention go beyond taking advantage of the rapid growth of tumors. It exploits important quantitative differences in the levels of enzymes between neoplastic and normal tissue. CldUTP, a metabolite product of CldC when administered in the presence of $H_4U$ is preferably formed in tumor tissue to result in tumor directed toxicity and radiosensitization. Because of the mode of radiosensitization of pyrimidine analogs differs from that of hyperthermy and hypoxic cell sensitizers, our procedure and strategy may be used with those modalities in radiation therapy.

What is claimed is:

1. A method of sensitizing susceptible tumor tissue to x-ray, gamma, beta, ultraviolet light, or near visible light (313 nm) radiation, said tissue having elevated levels of cytidine deaminase, deoxycytidine kinase, dCMP deaminase, or combinations thereof, which comprises administering to a patient having such tissue a radiation-sensitizing amount of a deoxycytidine compound of the formula:

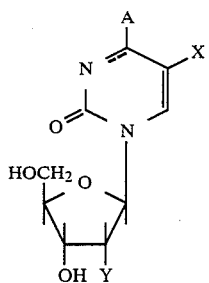

wherein A is —NH₂; X is chloro; Y is hydrogen — — — — is a double bond; and a systemic deamination-preventing amount of a deamination inhibitor selected from the group containing of tetrahydrouridine and 2'-deoxytetrahydrouridine.

2. A method according to claim 1, wherein 5-fluoro-2'-deoxyuridine, 5-fluoro-2'-deoxycytidine plus tetrahydrouridine, N-(phosphonacetyl)-L-aspartate, or combinations thereof, is administered to the patient, prior to the administration of the deoxycytidine compound.

3. A method according to claim 1, wherein the amount of the deoxycytidine compound is from about 200 to 2,500 mg/kg of body weight.

4. A method according to claim 1, wherein the amount of the deamination inhibitor is from about 10 to about 200 mg/kg of body weight.

5. The method of claim 1, wherein the ratio of the deamination inhibitor to the deoxycytidine compound is about 1:30 to about 1:5.

6. A method of treating a patient having tumor tissue which is susceptible to radiation therapy and which contains elevated levels of cytidine deaminase, deoxycytidine kinase, dCMP deaminase, or combinations thereof, which comprises:

administering to the patient a therapeutically effective amount of 5-fluoro-2'-deoxyuridine, 5-fluoro-2'-deoxycytidine and tetrahydrouridine, N-(phosphonacetyl)-L-aspartate, or combinations thereof; and then administering to the patient a radiation-sensitizing amount of a deoxycytidine compound of the formula:

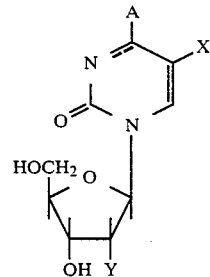

wherein A is a —NH₂; X is chloro; Y is hydrogen; and — — — — is a double bond, and thereafter exposing the tumor tissue to an amount of x-ray, gamma, beta, ultraviolet light or near visible light (313 nm) radiation sufficient to kill a substantial portion of the tumor tissue without disturbing the normal tissue surrounding the tumor tissue.

7. A method according to claim 6, wherein the tumor tissue is irradiated with x-rays or gamma rays.

8. A method according to claim 6, wherein the said deoxycytidine compound of Formula I is 5-chloro-2'-deoxycytidine.

9. A pharmaceutical composition for sensitizing tumor tissue susceptible to radiation therapy and which contains elevated levels of cytidine deaminase, deoxycytidine kinase, dCMP deaminase, or combinations thereof, comprising a radiation sensitizing effective amount of a deoxycytidine compound of the formula:

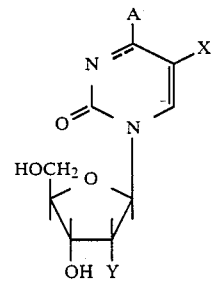

wherein A is —NH₂; X is chloro; Y is hydrogen; and — — — — is a double bond, and at least one deamination inhibiting effective amount of a deamination inhibitor selected from the group consisting of tetrahydrouridine and 2'-deoxytetrahydrouridine.

10. A composition according to claim 9, wherein the deoxycytidine compound is 5-chloro-2'-deoxycytidine.

11. A composition according to claim 9, wherein the weight ratio of the deamination inhibitor to the deoxycytidine compound is from about 1:30 to 1:5.

* * * * *